United States Patent [19]

Williams

[11] 4,424,817
[45] Jan. 10, 1984

[54] SYRINGE WITH MEANS FOR AUTOMATICALLY SEALING A BLOOD SAMPLE WITHIN THE SYRINGE

[75] Inventor: Charles D. Williams, Rolling Hills Estate, Calif.

[73] Assignee: Marquest Medical Products, Inc., Englewood, Colo.

[21] Appl. No.: 279,441

[22] Filed: Jul. 1, 1981

[51] Int. Cl.³ ............................................... A61B 5/14
[52] U.S. Cl. ................................................... 128/766
[58] Field of Search ............... 128/220, 237, 218 P, 128/218 M, 763–767

[56] References Cited

U.S. PATENT DOCUMENTS

| | | | |
|---|---|---|---|
| 718,979 | 1/1903 | Campbell | 128/218 P |
| 984,037 | 2/1911 | Sheets | 128/237 |
| 1,643,531 | 9/1927 | Wolf . | |
| 2,263,865 | 11/1941 | Bailen | 128/215 |
| 2,549,417 | 4/1951 | Brown | 128/272 |
| 2,735,428 | 2/1956 | Huber | 128/218 |
| 3,290,946 | 12/1966 | Pursell | 75/423 |
| 3,291,128 | 12/1966 | O'Neil | 128/218 |
| 3,326,215 | 6/1967 | Sarnoff et al. | 128/220 |
| 3,557,778 | 1/1971 | Hughes | 128/764 X |
| 3,566,859 | 3/1971 | Schwartz | 128/765 |
| 3,656,480 | 4/1972 | Rubricius | 128/218 |
| 3,736,932 | 6/1973 | Satchell | 128/218 |
| 3,809,298 | 5/1974 | Harris | 222/386 |
| 3,886,930 | 6/1975 | Ryan | 128/2 |
| 3,930,492 | 1/1976 | Hatsuno | 128/2 |
| 3,938,513 | 2/1976 | Hargest | 128/218 |
| 3,960,139 | 6/1976 | Bailey | 128/2 |
| 4,008,718 | 2/1977 | Pitesky | 128/234 |
| 4,057,052 | 11/1977 | Kaufmann | 128/2 |
| 4,299,238 | 11/1981 | Baidwan et al. | 128/763 |

Primary Examiner—William R. Dixon, Jr.
Assistant Examiner—Nancy A. B. Swisher

[57] ABSTRACT

A syringe for drawing gas-free blood samples is disclosed having a sliding assembly operatively connected to an elongated hollow plunger rod, both the sliding assembly and the plunger rod slideably received within the interior of the tubular body, which is connected to an hypodermic needle. The sliding assembly has longitudinal grooves formed along a portion of the length therein which are in fluid communication with inwardly directed smaller cross section radial channels formed in the sliding assembly. The channels are in further fluid communication with a passageway along the longitudinal axis of the sliding assembly and the hollow elongated plunger. Means for preventing the passage of air back into the syringe once the blood level has reached that position are provided. Means for sealing the blood into the syringe are also provided.

13 Claims, 6 Drawing Figures

U.S. Patent    Jan. 10, 1984    4,424,817
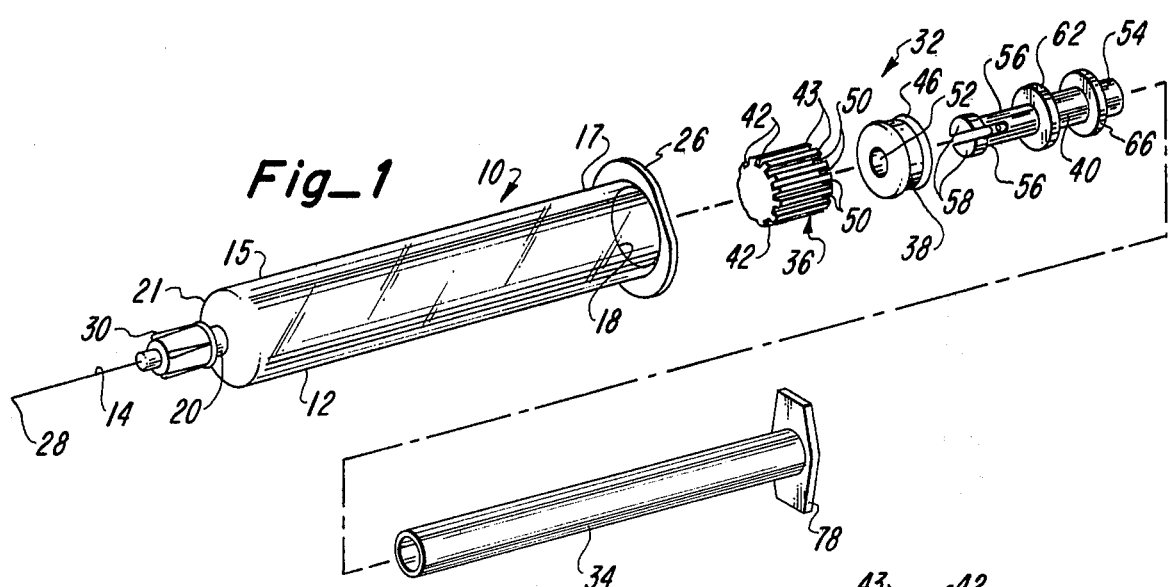
Fig_1
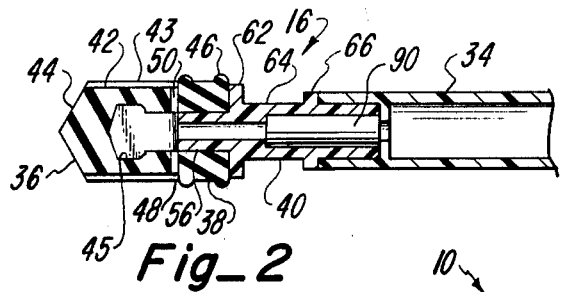
Fig_2
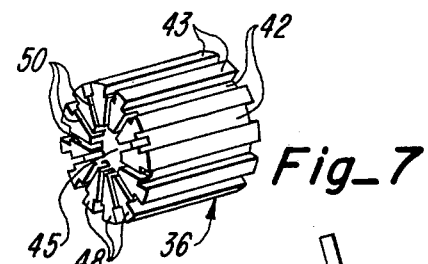
Fig_7
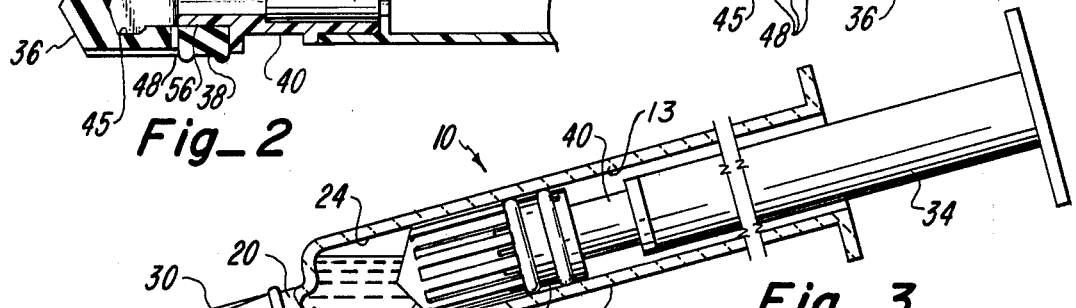
Fig_3
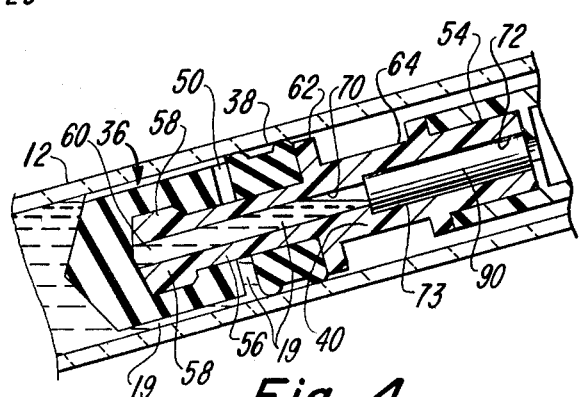
Fig_4
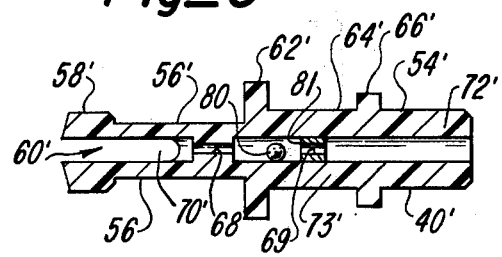
Fig_5
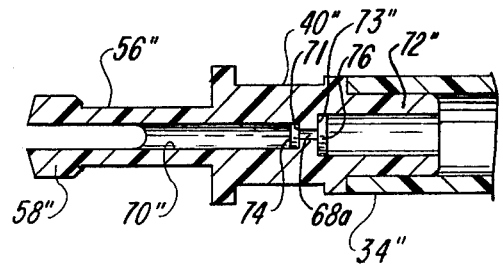
Fig_6

SYRINGE WITH MEANS FOR AUTOMATICALLY SEALING A BLOOD SAMPLE WITHIN THE SYRINGE

BACKGROUND OF THE INVENTION

1. Field of Invention

This invention relates generally to syringe devices adapted to collect blood samples. More particularly, the invention relates to syringes capable of collecting blood samples that are purged of any gaseous contaminants.

2. Description of the Prior Art

Syringe devices conventionally include tubular bodies receiving pistons or sealing members connected to plungers. The syringe devices have been adapted to discharge trapped air from an interior chamber, defined by the position of the sealing member, into which chamber a medicament or blood sample is drawn. The structures, and even the specific purposes for removing the air, vary widely.

The time-honored technique for removing air from the interior chamber of a syringe is simply inverting the syringe and squeezing out a portion of the aqueous contents of the interior chamber, presumably with any trapped air. This method is somewhat effective in the preparation of medicaments for injection into a patient, but the indiscriminate discharge of blood in a hospital environment is unsanitary.

There are many prior art syringe devices that utilize some type of vent between the interior chamber and the atmosphere. What differs among the various syringe devices is the manner in which the vent, once formed, is closed at the proper time. An example of a blood-gas syringe device is seen in U.S. Pat. No. 4,206,768 to Bailey, that patent having common ownership with the present application. In the Bailey patent, a vent is formed by a string or thread passed across the sealing member. The string is adapted to be manually wound onto a plunger, sealing the vent, after the blood sample is obtained and the gas has been purged across the sealing member via the vent. The plunger is rotatably connected to the sealing member.

Hollow plungers are one type of structure used for venting air from the interior chamber to ambient pressure. Such a device is seen in U.S. Pat. No. 1,643,531 to Wolf, wherein a sample of medicament is drawn, air is purged along the hollow plunger, the vent through the plunger is capped, and the syringe is utilized to inject the contents of the syringe. This specific device is not adapted for use in blood-gas analysis because capping the plunger does not seal off air within the plunger from the sample. Wolf also requires capping the plunger for effective use, as opposed to self-sealing of the vent at the interior chamber. An extra manual step is required in virtually all of the syringe devices to seal a vent once made.

Filter elements are commonly utilized in syringe devices, primarily for purposes of preventing particulate matter from entering the medicament or the patient. To Applicant's knowledge, however, filters have not been utilized to seal the vent, within a certain range of pressures, of a blood-gas syringe, though hydrophobic filters, which allow gas to pass until they are wetted, as by blood, are commercially available. Hydrophobic plastic is suggested as a material for an integral plunger-sealing member in U.S. Pat. No. 3,656,480, to Rubricius, but the hydrophobic properties are not necessary for the purposes of the invention.

Use of fabric filter elements to inhibit the flow of blood are known. U.S. Pat. Nos. 3,960,139 and 3,978,846 to Bailey disclose filters that partially, and preferably totally, restrict the flow of blood after gases have been allowed to flow therethrough.

The prior art does not show a syringe device for obtaining a gas-free blood sample that automatically seals off the blood sample obtained once predetermined conditions are reached. The conditions relate to volume of the blood sample and purging of air associated with the blood sample.

A copending application having Ser. No. 359,292, filed Mar. 18, 1982, entitled "Syringe With Means For Allowing Passage Of Air While Preventing Passage Of Blood To Obtain Gas-Free Blood Sample", which is a continuation of Ser. No. 279,453, filed July 1, 1981, entitled "Syringe With Hydrophobic Filter", now abandoned does show automatic sealing off of the blood sample within the syringe by use of a hydrophobic filter. Though the apparatus disclosed in that application is fairly effective, as long as breakthrough pressure is not exceeded, in utilizing a hydrophobic filter to stop the flow of blood across the filter once the filter is wetted by the blood, the filter will not stop the passage of air across the filter. Thus, unless the blood sample is obtained in such a manner that the interior chamber of the syringe is totally filled with blood, air can flow back across the hydrophobic filter into the interior chamber and come into contact with the blood sample. Even when no bubbles of air are initially present, as a result of the syringe being packed in ice for transport to an area where testing is to be performed, the blood cools and therefore contacts, permitting air to cross the filter.

Because of its simplicity, many hospitals and doctors still utilize the expulsion method with medicaments, but a need has existed for a simple, effective yet inexpensive, syringe device for obtaining a blood sample free of air contamination.

OBJECTS AND SUMMARY OF THE INVENTION

The principal object of the present invention is to provide an inexpensively manufactured syringe device for obtaining a gas-free blood sample.

It is a related object of the present invention to provide a syringe device that can be easily operated to obtain a gas-free blood sample.

It is a further related object of the present invention to provide a syringe device for obtaining a gas-free blood sample that automatically seals off the blood sample when a blood sample purged of air is collected.

Another object of the present invention is to provide means for preventing recontamination of a blood sample by air.

In accordance with the objects of the invention, a syringe having a hollow, tubular body with an open end and an end wall having means for connection to an hypodermic needle is provided. The open end of the tubular body receives a plunger assembly including a sliding assembly operatively connected to a plunger rod. The sliding assembly includes a plunger front, plunger rear and plunger body. An interior chamber is defined between the end wall of the tubular body and a foward end of the sliding assembly. It is within the interior chamber that a blood sample is collected.

The generally cylindrically shaped plunger front has longitudinal grooves formed parallel to the longitudinal axis of the tubular body. A mating recess coaxial with the longitudinal axis of the tubular body is formed at the rearward end of the plunger front. Channels extend radially from the mating recess to communicate with the longitudinal grooves. The generally cylindrically shaped plunger rear has a pair of peripheral lips, which lips are adapted to contact the interior surface of the tubular body abutted against the plunger front. The plunger rear has a central bore therethrough aligned with the mating recess.

The plunger body has a hollow portion along the length thereof and two forwardly extending arms having a space therebetween. Each arm has a short radial flange at the termination thereof. The arms and flange are passed through the bore of the plunger rear and into the mating recess of the plunger front to thereby join the three components of the sliding assembly together. The rearward end of the hollow plunger body is attached to the plunger rod, which is also hollow. An absorbent filter cartridge is disposed across the hollow portion of the plunger body. The filter can be an organic fiber, like pqper.

Insertion of the hypodermic needle into an artery of a patient therefore allows blood to fill the interior chamber. Blood then substantially fills the interior chamber and expels air along longitudinal grooves and across radial channels. The channels are in fluid communication with the space between the arms of the plunger body.

As air followed by blood is urged under the blood pressure of the individual through the hollow plunger body, the air and then blood encounters the filter, which filter allows both air and blood to pass until such time as the blood contacts the filter. The filter eventually prevents further flow and blood flow stops, and a gas-free blood sample is obtained.

In a first alternative embodiment, a buoyant plug or check valve replaces the filter cartridge to clog the hollow portion of the plunger body as the blood level rises. In a second alternative embodiment, an hydrophilic filter in combination with an hydrophobic filter replaces the filter cartridge. Once wetted by blood, the hydrophilic filter prevents the plunger of air across the filter. The flow of blood and air continues until the hydrophobic filter is wetted, at which time flow of blood is stopped.

BRIEF DESCRIPTION OF THE DRAWINGS

FIG. 1 is an exploded perspective view of the syringe device of the present invention.

FIG. 2 is a fragmentary full sectional view of a sliding assembly and connected plunger rod of the invention seen in FIG. 1.

FIG. 3 is a fragmentary side elevational view of the invention seen in FIG. 1 filling with blood.

FIG. 4 is a fragmentary full sectional view of a plunger body of the invention shown in FIG. 1 filling with blood.

FIG. 5 is a sectional view of a first alternative embodiment of the plunger body.

FIG. 6 is a sectional body of a second alternative embodiment of the plunger body.

FIG. 7 is a perspective view taken in a direction opposite to the view of FIG. 1 showing a plunger front of the invention seen in FIG. 1.

DESCRIPTION OF THE PREFERRED EMBODIMENTS

A syringe device 10 for obtaining a blood sample from an individual's artery under the force of the individual's blood pressure is seen in FIGS. 1 and 3. The syringe 10 collects the blood sample in such a manner that all air is purged from the blood sample and the blood flow within the syringe is stopped. Both of these functions occur automatically at predetermined positions along a blood and air flow passageway 19 through the syringe (FIG. 4). The syringe includes an elongated tubular body 12 having a bore 13, which body connects in a conventional manner to an hypodermic needle 14 at a forward end 15 of the tubular body 12. The tubular body slideably receives a plunger assembly 16 (FIG. 2) through an open end or opening 18 at a rearward end 17 of the tubular body and cooperates with the body in defining a selectively variable volume interior chamber 24.

The tubular body 12 is of hollow cylindrical configuration and is formed of a transparent material like glass or disposable plastic. This type of tubular body 12 is currently commercially available in large quantities. A relatively short extension 20, compared to the length of the tubular body 12, projects forwardly from an end wall or end member 21 disposed at the forward end 15 of the tubular body 12. The extension 20 has a bore 22 therethrough, which bore is coaxial with the longitudinal axis of the tubular body 12. The bore 22 provides a pathway from the needle 14 to the interior chamber 24 of the tubular body 12.

The interior chamber 24 of the tubular body 12 is defined as the variable volume between the end wall 21 and the forwardmost end of the plunger assembly 16, as the plunger assembly is slid to various positions along the length of the tubular body. The interior chamber is adapted to contain the collected blood sample and therefore must remain free of gaseous contaminants. The opening 18 leads to a constant cylindrical chamber along the length of the tubular body 12 from the rearward end 17 to the forward end 15. A radially outwardly extending peripheral flange 26 circumscribes the opening 18 to facilitate the pulling or retracting of the plunger assembly 16, or alternatively the pushing or insertion of the plunger assembly, along the length of the tubular body 12.

The needle or cannula 14 is also of conventional configuration (FIGS. 1 and 3). A tip 28 is adapted to be inserted into the artery of a patient. At the opposite end of the needle 14 from the tip is located a hub 30, which hub is frictionally connected to the extension 20. Once the tip is inserted into an artery of the patient, the lumen of the needle 14 allows blood to flow under blood pressure into the bore 22 of the extension 20 and finally into the interior chamber 24.

The plunger assembly 16 (FIGS. 1 and 2) includes a forward sliding assembly 32 operatively connected to a trailing elongated hollow plunger rod 34. The sliding assembly 32 is further subdivided into three components. A plunger front 36 is positioned at the forwardmost end of the sliding assembly. A plunger rear 38 is held adjacent to the plunger front by a plunger body 40 which passes through both the plunger front and the plunger rear to thereby interconnect all three components in a manner to be described hereinafter. The trailing end of the plunger body 40 is pressed onto the interior of the hollow plunger rod 34 to complete the plunger assembly 16. It will be seen that the entire plunger assembly provides the blood and air flow passageway 19 from the interior chamber 24 to the ambient atmosphere. Blood is allowed to traverse the passageway 19 until such time as it is automatically sealed off within the plunger assembly in a manner to be described later. Air is vented to the atmosphere and prevented from re-entering the interior chamber 24 and thereby contaminating the blood sample, again, as will be described.

The plunger front 36 (FIGS. 1 and 7) of the sliding assembly 32 is of generally cylindrical configuration. A portion of the outer surface of the plunger front 36 intimately contacts the interior surface of the tubular body 12. The outer surface of the plunger front has a plurality of longitudinal grooves of passageways 42 extending from the forward end of the plunger front to the plunger rear 38, as seen in FIG. 2. The grooves 42 are separated by longitudinally extending teeth 43, which teeth actually contact the interior surface of the tubular body 12. The longitudinal grooves form a first part of the blood and air flow passageway 19 from the interior chamber 24 to the ambient atmosphere.

The forward or inserted end of the plunger front 36 terminates in a conically shaped head 44, which head defines the interface between the plunger assembly 16 and the interior chamber 24. A mating recess 45 of T-shaped cross section is formed at the rearward end of the plunger front 36, which recess is adapted to form a snap connection with the forward end of the plunger body 40, in a manner to be discussed shortly.

A plurality of radially extending channels or passageways 50 (FIG. 7) are formed in the rearward end of the plunger front 36 to provide fluid communication between the mating recess 45 and the longitudinal grooves 42. The channels are of substantially less cross sectional area along the blood and air flow passageway 19 than the grooves 42, a magnitude of approximately one teeth being preferable. The plunger front is preferably constructed from a resilient polymeric material.

The plunger rear 38 is also of generally cylindrical configuration and formed from a like resilient polymeric material. The forward end of the plunger rear 38 abuts against the rearward end of the plunger front 36. A pair of peripheral lips 46 extend circumferentially around the plunger rear, providing continuous contact, and therefore an hermetic seal, with the interior surface of the tubular body 12. The forwardmost lip 46 seals off the passage of blood and air, while the rearwardmost tip 46 stabilizes and aligns the sliding assembly 32. A face 48 of the plunger rear 38 abuts against the plunger front 36. A longitudinal bore 52 passes through the plunger rear.

The plunger body 40 (FIGS. 1 and 4) is formed of transparent plastic and includes an elongated hollow portion 54. The forward end includes a pair of bifurcated forwardly extending arms 56, each arm having a small semi-circular flange 58 projecting radially from the end of the arm toward the interior surface of the tubular body 12 as the plunger body is aligned along the longitudinal axis of the tubular body 12. A space 60 (FIG. 4) is therefore defined between the arms 56. The space 60 is in fluid communication with the hollow interior of the plunger body 40. A disc-shaped outwardly extending first stop 62 integrally connected to the elongated portion 54 has an edge that is slightly smaller than the interior surface of the tubular body 12 when the entire sliding assembly 32 is inserted into the tubular body. An intermediate portion 64 of the elongated portion 54 spaces the first stop from a smaller disc-shaped stop 66 located rearwardly of the first stop.

As has been previously stated, the plunger body 40 is hollow along the entire length thereof. A forward hollow portion 70 (FIGS. 2 and 4) extends rearwardly from the space 60 between the arms 56 toward the rearward end of the plunger body 40. The forward hollow portion 70 terminates at a longitudinal position in the area of the intermediate portion 64 of the elongated portion 54. A rearward hollow portion 72, of a slightly larger diameter than the forward hollow portion, intersects the forward hollow portion 70 and extends the balance of the length of the plunger body 40. At the intersection between the forward hollow portion 70 and the rearward hollow portion 72, a rearward seat 73 is formed. An absorbent filter cartridge 90 is positioned against the rearward seat 73. The filter 90 is formed from an organic fiber material, i.e. paper, and substantially fills the volume presented by the rearward hollow portion 72. The plunger rod 34 is press fitted onto the elongated portion 54 of the plunger body 40 and against the stop 66. Radially inturned shoulders of the hollow plunger rod retain the filter 90 within the hollow portion 72.

The sliding assembly 32 is joined together by first inserting the arms 56 and flanges 58 of the plunger body 40 through the bore 52 of the plunger rear 38. The rearward end of the plunger rear is placed flush against the first stop 62 of the plunger body 40.

The arms 56 and flanges 58 of the plunger body 40 project from the mounted plunger rear 38 a short distance in a forward direction. The arms and flanges form a shape generally conformable to the mating recess 45 at the rearward end of the plunger front 36 (FIG. 2). The arms 56 have a certain degree of resilience so that when placed adjacent each other, the flanges 58 can enter the mating recess. Once the flanges and arms fit into the mating recess, a positive connection between the plunger front 36 and the plunger body 40 is established, the plunger rear 38 being held in position therebetween. The radial channels 50 will be seen to fluidly communicate with the space 60 between the arms 56 to thereby form a part of the blood and air passageway 19.

The plunger rod 34 is hollow along the entire length thereof, forming the final portion of the blood and air passageway 19, though as will be seen, no blood enters the plunger rod 34. The plunger rod 34 has at the trailing end a finger grip 78 extending perpendicularly from a longitudinal axis of the plunger rod. The forward end of the rod 34 is attached to the rearward end of the plunger body 40 of the sliding assembly 32, as previously mentioned. The plunger assembly 16 in this condition is complete and can be inserted into the opening 18 in the tubular body 12, ready for use.

The operation of the syringe 10 can be summarized as the obtaining of a blood sample which is purged of gas, while at the same time automatically sealing the blood sample within the syringe. The only manual operations necessary are the insertion of the needle 14 into the artery of the individual and the setting of the sliding assembly 32 to establish the volume of the blood sample.

Once the needle 14 is inserted into the artery, blood flows through the lumen of the needle and the bore 22 of the extension 20 into the interior chamber 24 (FIG. 3). As the blood sample continues to fill the interior chamber 24, it ultimately contacts the head 44 of the plunger front 36, which head defines the interface between the interior chamber and the sliding assembly 32. The conical configuration of the head 44 reduces the angle of incidence relative to the rising blood sample and also matches the shape of the end wall 21 and allows maximum discharge of the sample for analysis when the syringe 10 is emptied. The blood can either flow through the longitudinal grooves 42, or fill the interior chamber. Because of the higher pressure required to move blood along the relatively small area of the grooves, as well as the fact that the surface tension of the blood is not easily broken because of the conical head, the blood will tend to rise along the head and fill the interior chamber 24 before it traverses the grooves 42 in the plunger front 36 to any great extent.

As the interior chamber 24 is completely filled, the blood sample is essentially defined as to volume. It remains only to purge all air from the sample and seal the sample off within the syringe 10.

The blood continues to flow under the individual's blood pressure along the longitudinal grooves or passageways 42 in the plunger front 36. It should be noted that, regardless of the filling angle, air will be purged from the interior chamber 24 because the grooves 42 are at the outer edge of the plunger front. Air can not be trapped against the interior surface of the tubular body 12. This feature considerably eases operation of the syringe device 12. At the rearward end of the plunger front the blood continues to flow along the blood and air passageway 19 between the interior chamber and the ambient atmosphere by flowing along the radial channels 50 of the plunger front 36. The restriction of the radial channels 50 will cause slight pressure increases with respect to the longitudinal grooves 42. The forwardmost peripheral lip 46, which is rearward of the channels formed on the plunger front, will insure that no blood flows rearwardly beyond the lip. The blood flows evenly regardless of the filling angle radially inward to the longitudinal axis of the plunger assembly to the preselected position defined by the space 60. This flow of blood down the channels occurs essentially simultaneously because the blood will fill the larger volumes of the grooves 42 until the grooves are filled with blood, before traversing the smaller channels.

Blood fills the space 60 and is then forced along the forward hollow portion 70 of the plunger body 40 until such time as it contacts the filter 90, at which time the filter colors red and the operator knows a gas free blood sample has been obtained. The filter is, to an extent, permeable to both aqueous blood and air. Eventually, blood flow will be greatly restricted or stopped due to the very small cross sectional area between fibers of the filter 90. The required pressure for blood passage will therefore be greater than the available arterial pressure. The capillary action of the filter 90, as well as its length, must be set so as to stop the blood flow along the length of the filter. These parameters can easily be determined from the blood density.

Therefore, it is seen that as the blood level rises within the forward hollow portion 70, the filter 90 absorbs some of the aqueous blood. Eventually, the hollow forward portion 70 is completely filled with blood and air has been completely purged from the blood and air passageway 19 forward of the filter 90. It remains only to seal the blood itself within the syringe 10, which occurs when the blood pressure will not pass the blood through the filter 90. Alternatively, when the filter 90 is contacted, the needle 14 can be withdrawn. Even if a small amount of air is retained in the blood and air flow passageway 19, it cannot re-enter the interior chamber 24 to affect the analysis.

A preselected dosage of anticoagulant, like sodium heparin, can be placed in the interior chamber 24 prior to a blood sample being drawn. This provides for automatic treatment of the blood sample to prevent coagulation and allow greater time periods for performing blood-gas analysis testing.

In a first alternative embodiment (FIG. 5), like parts being given a prime suffix, a buoyant plug or spherical ball valve 80 is positioned in the rearward hollow portion 72'. The plug is made of Styrofoam, or other material with a specific gravity less than blood, and would have a diameter of approximately twenty thousandths to forty thousandths of an inch. The plug would replace the filter 90. The forward hollow portion 70' is shortened and replaced in part by a small bore 68 against which the plug can seat. A rearward insert 81 has a like small bore 69. The plug is therefore positioned between the two bores 68 and 69 and is adapted to seal against the insert 81 as the passageway 19 fills with blood. As blood fills the passageway 19, the plug 80 is raised. The blood plug will seal the small bore 68, sealing off the blood sample purged of contaminates.

As the syringe 10' is withdrawn from the patient, the needle 14' is corked and the syringe is placed in ice. The blood volume will contract as the blood cools. The plug 80 seats against the bore 68 of the forward hollow portion 70', preventing air from re-entering the forward hollow portion.

A second alternative embodiment (FIG. 6), like parts being given a double prime suffix, also replaces the filter 90 with an hydrophilic filter 74 followed by a hydrophobic filter 76. The plunger body 40" includes a small bore 68a interconnecting the forward hollow portion 70" and rearward hollow portion 72". The hydrophilic filter 74 fits against a forward seat 71, while the hydrophobic filter 76 fits against the rearward seat 73".

As blood contacts the hydrophilic filter 74, the material used will allow air to pass until completely wetted. Once wetted, air will not pass unless the pressure across the hydrophilic filter exceeds the water bubble point pressure, approximately twenty-two pounds per square inch. The blood fills the bore 68a and then contacts the hydrophobic filter 76. When the hydrophobic filter 76 is wetted, it is impermeable to aqueous blood, unless pressures exceed the water breakthrough pressure of twenty pounds per square inch. Both filters 74 and 76 can be obtained from Gelman Sciences, Inc., 600 South Wagner Road, Ann Arbor, Michigan, 48106, under the trademarks "VERSAPORE 200" and "VERSAPORE 200H", respectively.

Although the present invention has been described with a certain degree of particularity, it is understood that the present disclosure has been made by way of example, and that changes in detail and structure may be made without departing from the spirit thereof.

What is claimed is:

1. A syringe device for obtaining a blood sample comprising in combination:
    a tubular body having an interior surface defining a bore, said tubular body having an opening at a rearward end thereof and an end wall at a forward end thereof, said end wall having connection means for connecting a needle to the tubular body;
    a sliding assembly slideably received within said opening in slideable engagement with the interior surface of said tubular body with means for providing a seal between said sliding assembly and said tubular body, said sliding assembly having at least one longitudinal passageway and at least one radial passageway, said longitudinal passageway in fluid communication with said radial passageway, said radial passageway extending radially inward to a preselected position, said radial passageway being contiguously adjacent to said means for providing a seal so that, regardless of the position of the syringe device when obtaining a blood sample, virtually no gas will be present adjacent to said radial passageway for movement back into the collected blood sample;

a hollow elongated plunger rod having a plunger passageway, said rod connected to said sliding assembly, said hollow plunger rod and said sliding assembly being movable to define an interior chamber in said bore for collecting the blood sample, said plunger rod being in fluid communication with said radial passageway whereby fluid communication is provided between said interior chamber and the ambient atmosphere through said longitudinal passageway, said radial passageway, and said plunger passageway; and means associated with one of said passageways for allowing the passage of air and restricting the passage of blood along said passageways.

2. The invention defined in claim 1 wherein said longitudinal passageway and said radial passageway are contiguously adjacent to provide a predetermined path for fluid into said plunger passageway.

3. The invention defined in claim 1 wherein said interior chamber has a larger transverse cross sectional area relative to the flow of fluid than the transverse cross sectional area of said longitudinal passageway.

4. The invention defined in claim 1 wherein said longitudinal passageway has a substantially larger transverse cross sectional area relative to the flow of fluid than the transverse cross sectional area of said radial passageway.

5. The invention defined in claim 1 wherein said longitudinal passageway has a cross sectional area such that the pressure required to force blood into the interior chamber is less than that pressure required to force blood into the longitudinal passageway, and the pressure required to force blood into the longitudinal passageway is less than that pressure required to force blood into the radial passageway.

6. The invention defined in claim 1 wherein said sliding assembly further includes:

a generally cylindrical plunger front having said longitudinal passageway and radial passageway formed therein, said plunger front further having a mating recess formed therein;

a generally cylindrical plunger rear abutted against said plunger front, said plunger rear having sealing means for hermetically sealing the interior surface of said tubular body and a bore therethrough; and connection means for joining said plunger rear to said plunger front by passing through said bore into said recess, said connection means providing for fluid communication between said longitudinal and radial passageways and said plunger passageway.

7. The invention defined in claim 6 wherein said connection means further includes:

an elongated plunger body having a pair of forwardly projecting arms separated by a space, each of said arms having at the forwardmost end thereof outwardly directed flange portions, said arms adapted to pass through said bore in said plunger rear into said mating recess in said plunger front, said plunger body further having a hollow portion extending from the space between said arms to the rearward end of said plunger body, said plunger body further having a first stop adapted to abut against said plunger rear and a second stop adapted to abut against said plunger rod.

8. The invention defined in claim 7 wherein said means for allowing the passage of air and restricting the passage of blood further includes:

a plunger body having a small bore along the portion of the length thereof compared to said hollow portion; and a buoyant plug adapted to block said bore as said plunger body fills with blood.

9. The invention defined in claim 7 wherein said means for allowing the passage of air and restricting the passage of blood further includes:

absorbent means located at a preselected position along a preselected length of said hollow portion for allowing passage of air and a restricted passage of blood.

10. The invention defined in claim 1 wherein said means for allowing the passage of air and restricting the passage of blood includes: filter means joined to said sliding assembly at said plunger rod for allowing the passage of air and restricting the passage of blood and also preventing air flow in a reverse direction back into said interior chamber.

11. A syringe device for obtaining a blood sample comprising in combination:

a tubular body having an interior surface defining a bore, said tubular body having an opening at a rearward end thereof and an end wall at a forward end thereof, said end wall having connection means for connecting a needle to the tubular body;

a sliding assembly having means for providing a seal between said sliding assembly and said tubular body and a plunger front having at least one longitudinal passageway and at least one radial passageway formed therein, a plunger rear abutting against said plunger front, and a hollow plunger body having a pair of bifurcated forwardly projecting arms having a space therebetween, said plunger body operatively connecting said plunger front to said plunger rear along an axis coaxial with the longitudinal axis of said tubular body, said sliding assembly being slideably received within said open end for slideable engagement with the interior surface of said tubular body, said sliding assembly being movable to define an interior chamber in said bore for collecting the blood sample, said plunger front having a conical head projecting forwardly into said tubular body, said longitudinal passageway providing fluid communication from said interior chamber to said radial passageway, said radial passageway perpendicularly intersecting said axis of said sliding assembly, said space of said plunger body being in fluid communication with said radial passageway, said radial passageway being contiguously adjacent to said means for providing a seal so that, regardless of the position of the syringe device when obtaining a blood sample, virtually no gas will be present adjacent to said radial passageway for movement back into the collected blood sample;

a hollow elongated rod defining a plunger passageway, said rod connected to and in fluid communication with said plunger body; and means associated with one of said passageways for automatically allowing the passage of air and restricting the passage of blood along said passageway.

12. A syringe device for obtaining a blood sample comprising in combination:

a tubular body having an interior surface defining a bore, said tubular body having an opening at a rearward end thereof and an end wall at a forward end thereof, said end wall having connection means for connecting a needle to the tubular body; and a plunger assembly slideably received within said opening of said tubular body, a portion of said plunger assembly sealably contacting the interior surface of said tubular body, said plunger assembly being movable to define an interior chamber in said bore for collecting the blood sample, said plunger assembly having a longitudinal passageway in fluid communication with said interior chamber, a radial passageway in fluid communication with said longitudinal passageway and a plunger passageway in fluid communication with said radial passageway and the ambient atmosphere, wherein the pressure required to force blood into the interior chamber is less than that pressure required to force blood into said longitudinal passageway and the pressure required to force blood into said longitudinal passageway being less than that pressure required to force blood into said radial passageway, thereby selectively expelling air at each passageway, said radial passageway being contiguously adjacent to said means for providing a seal so that, regardless of the position of the syringe device when obtaining a blood sample, virtually no gas will be present adjacent to said radial passageway for movement back into the collected blood sample; and means associated with one of said passageways for allowing the passage of air and restricting the passage of blood along said passageways.

13. A syringe device for blood samples comprising in combination:

a tubular body having an interior surface defining a bore, said tubular body having an opening at one end thereof and an end wall at another end thereof, said end wall having connection means for connecting a needle to the tubular body;

a sliding assembly slideably received within said opening in slideable engagement with the interior surface of said tubular body with means for providing a seal between said sliding assembly and said tubular body, a plunger rod operatively connected to said sliding assembly, said plunger rod and said sliding assembly being movable to define an interior chamber in said bore for collecting the blood sample, said connected sliding assembly and plunger rod having at least one blood and air passageway providing air communication between said interior chamber and the ambient atmosphere, said blood and air passageway further defining a fluid flow path from the interior chamber to the ambient atmosphere; and means for allowing the passage of air and restricting the passage of blood, said means for allowing the passage of air and restricting the passage of blood including a filter being connected to said sliding assembly or said plunger rod across said blood and air passageway to allow air to flow out of said interior chamber but to restrict blood from flowing out of said interior chamber;

and means for preventing air flow in a reverse direction back into said interior chamber, said means for preventing including a filter joined to said sliding assembly or said plunger rod.

* * * * *